(12) United States Patent
Yoshida et al.

(10) Patent No.: US 8,347,828 B2
(45) Date of Patent: Jan. 8, 2013

(54) DEVICE AND METHOD FOR DETECTING DEGRADATION OF FUEL FOR INTERNAL COMBUSTION ENGINE

(75) Inventors: Kaori Yoshida, Susono (JP); Satoshi Taniguchi, Numazu (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 481 days.

(21) Appl. No.: 12/680,005

(22) PCT Filed: Sep. 24, 2008

(86) PCT No.: PCT/IB2008/002486
§ 371 (c)(1),
(2), (4) Date: Mar. 25, 2010

(87) PCT Pub. No.: WO2009/040635
PCT Pub. Date: Apr. 2, 2009

(65) Prior Publication Data
US 2010/0211289 A1  Aug. 19, 2010

(30) Foreign Application Priority Data
Sep. 26, 2007  (JP) ................................. 2007-248893

(51) Int. Cl.
*G01N 21/00* (2006.01)
(52) U.S. Cl. ........ 123/1 A; 73/61.48; 356/409; 356/432; 701/114; 701/115
(58) Field of Classification Search .................. 123/1 A, 123/494, 381; 73/61.41, 53.01–53.07, 54.08; 356/70, 409–410, 326, 432–434, 442; 701/114, 701/115
See application file for complete search history.

(56) References Cited

U.S. PATENT DOCUMENTS

| | | | | |
|---|---|---|---|---|
| 3,750,635 A | * | 8/1973 | Hoffman et al. | 123/357 |
| 3,995,168 A | * | 11/1976 | Neuscheler et al. | 250/577 |
| 4,044,604 A | * | 8/1977 | Russ | 73/61.41 |
| 4,438,749 A | * | 3/1984 | Schwippert | 123/494 |
| 4,541,272 A | * | 9/1985 | Bause | 73/114.72 |
| 4,594,968 A | * | 6/1986 | Degobert et al. | 123/1 A |
| 4,703,732 A | * | 11/1987 | Wineland et al. | 123/406.47 |
| 4,706,630 A | * | 11/1987 | Wineland et al. | 123/478 |
| 4,918,979 A | | 4/1990 | Pearce et al. | |
| 4,971,015 A | * | 11/1990 | Gonze | 123/494 |
| 4,974,552 A | * | 12/1990 | Sickafus | 123/1 A |
| 5,090,817 A | * | 2/1992 | Ker et al. | 374/24 |
| 5,194,910 A | * | 3/1993 | Kirkpatrick et al. | 356/70 |

(Continued)

FOREIGN PATENT DOCUMENTS

JP  A-61-294337  12/1986

(Continued)

OTHER PUBLICATIONS

Feb. 11, 2009 Search Report issued in PCT/IB2008/002486.

(Continued)

*Primary Examiner* — Thomas Moulis
(74) *Attorney, Agent, or Firm* — Oliff & Berridge, PLC (57) ABSTRACT

A transmittance sensor that detects the optical transmittance of biofuel is provided on a fuel tank that stores biofuel to be supplied to an internal combustion engine. An ECU periodically acquires the optical transmittance detected by the transmittance sensor, and calculates the amount of change from the previous value. In addition, the ECU calculates a degradation index value indicating the degree of degradation of the biofuel by accumulating the amount of change.

17 Claims, 6 Drawing Sheets

U.S. PATENT DOCUMENTS

| | | | |
|---|---|---|---|
| 5,198,871 A * | 3/1993 | Hill et al. ................. 356/318 |
| 5,239,860 A * | 8/1993 | Harris et al. ............. 73/61.48 |
| 5,262,645 A | 11/1993 | Lambert et al. |
| 5,537,336 A * | 7/1996 | Joyce ........................ 702/108 |
| 6,121,628 A * | 9/2000 | Rising ........................ 250/573 |
| 7,297,963 B2 * | 11/2007 | Moses et al. ............. 250/459.1 |
| 7,367,223 B2 * | 5/2008 | Kettl et al. ............... 73/53.05 |
| 7,377,151 B1 * | 5/2008 | Magee ........................ 73/61.61 |
| 7,605,361 B2 * | 10/2009 | Uchida et al. ............. 250/227.25 |
| 8,260,560 B2 * | 9/2012 | Yoshikawa et al. ........ 702/24 |
| 2004/0137546 A1 | 7/2004 | Greenhill |
| 2005/0172700 A1 * | 8/2005 | Sugiura ........................ 73/61.48 |
| 2007/0163168 A1 | 7/2007 | Ramirez-Arizmendi et al. |
| 2008/0053202 A1 * | 3/2008 | Rohklin et al. ............. 73/61.41 |
| 2008/0165361 A1 * | 7/2008 | Kauffman .................... 356/402 |
| 2008/0282779 A1 * | 11/2008 | Noguchi et al. ............ 73/53.01 |
| 2009/0185188 A1 * | 7/2009 | Verdegan et al. ........... 356/442 |
| 2010/0020325 A1 * | 1/2010 | Osaki et al. ............... 356/436 |
| 2012/0047992 A1 * | 3/2012 | Sasai ........................ 73/23.32 |
| 2012/0140226 A1 * | 6/2012 | Pastusiak et al. ........... 356/410 |

FOREIGN PATENT DOCUMENTS

| | | |
|---|---|---|
| JP | A-63-55318 | 3/1988 |
| JP | A-2-185609 | 7/1990 |
| JP | A-10-305517 | 11/1998 |
| JP | A-2000-130240 | 5/2000 |
| JP | A-2003-139696 | 5/2003 |
| JP | A-2004-141134 | 5/2004 |
| JP | A-2004-197058 | 7/2004 |
| WO | WO 94/08226 A1 | 4/1994 |

OTHER PUBLICATIONS

Feb. 11, 2009 Written Opinion issued in PCT/IB2008/002486.

Jan. 14, 2010 International Preliminary Report on Patentability issued in PCT/IB2008/002486.

Sep. 25, 2009 Office Action issued in Japanese Patent Application No. 2007-248893 (with translation).

* cited by examiner

| DEGRADATION DEGREE Y | 5 | 6 | 7 | ... |
|---|---|---|---|---|
| FUEL PRESSURE CORRECTION COEFFICIENT | 1.1 | 1.2 | 1.3 | ... |

FIG. 7

| DEGRADATION DEGREE Y | 5 | 6 | 7 | ... |
|---|---|---|---|---|
| INJECTION AMOUNT CORRECTION COEFFICIENT | 1.1 | 1.2 | 1.3 | ... |

DEVICE AND METHOD FOR DETECTING DEGRADATION OF FUEL FOR INTERNAL COMBUSTION ENGINE

FIELD OF THE INVENTION

The present invention relates to device and method for detecting degradation of fuel for an internal combustion engine.

BACKGROUND OF THE INVENTION

Japanese Patent Application Publication No. 2000-130240 (JP-A-2000-130240) discloses a technique for diagnosing the degree of degradation of engine lubricating oil based on the difference in the light absorption loss at each of at least two monochromatic light sources with different wavelengths.

In recent years, there is growing tendency to use biofuels containing fuel produced from biomass as alternative fuels for vehicle engines. Since biofuels contain components having an unsaturated bond, they are easily oxidized as compared to conventional fuels. Oxidative degradation of biofuels produces acids which can corrode metal parts of the fuel system and so on. Also, biofuels can polymerize through reaction with oxygen and so on. When polymerization occurs, the viscosity of fuel increases, which may adversely affect the proper execution of fuel injection control.

When a vehicle has not been driven for along period of time or when the daily travel distance is so short that refueling is not done very often, the biofuel is left in the fuel tank for a long period of time. Then, degradation may proceed and adverse effects as describe above can occur. It is, therefore, desired to detect degradation of biofuel automatically in order to reliably prevent the adverse effects as describe above in vehicles using biofuel. However, a technique for detecting degradation of biofuel with high accuracy has not been established yet.

DISCLOSURE OF THE INVENTION

The present invention provides a device and a method for detecting degradation of fuel for an internal combustion engine capable of detecting degradation of biofuel with high accuracy.

A first aspect of the present invention, relates to a device for detecting degradation of fuel for an internal combustion engine. The device for detecting degradation of fuel includes: fuel supply means for supplying biofuel to an internal combustion engine; detection means for detecting an optical transmittance of the biofuel stored in the fuel supply means; change amount calculation means for acquiring the optical transmittance periodically and calculating the amount of change from the previous optical transmittance value to the current optical transmittance value; and degradation index value calculation means for calculating a degradation index value indicating the degree of degradation of the biofuel by accumulating the amount of change.

With this configuration, a degradation index value which indicates the degree of degradation of the biofuel can be calculated by acquiring an optical transmittance of the biofuel periodically and accumulating the amount of change from the previous optical transmittance value to the current optical transmittance value. Biofuels produce peroxides, oxide, polymerization products and so on in the process of degradation and change in color as the proportions of these compounds gradually change. As the color changes, the optical transmittance changes. Thus, since the degradation index value can be increased as the color indicating the degradation of the biofuel changes, the degree of degradation of the biofuel can be determined with high accuracy.

A second aspect of the present invention relates to a device for detecting degradation of fuel for an internal combustion engine. The device for detecting degradation of fuel include: fuel supply means for supplying biofuel to an internal combustion engine; detection means for detecting a color index value as an index of the color of biofuel stored in the fuel supply means; change amount calculation means for acquiring the color index value periodically and calculating the amount of change from the previous color index value to the current color index value; and degradation index value calculation means for calculating a degradation index value indicating the degree of degradation of the biofuel by accumulating the amount of change.

With this configuration, a degradation index value, which indicates the degree of degradation of the biofuel, can be calculated by acquiring a color index value as an index of color of the biofuel periodically and accumulating the amount of change from the previous optical transmittance value to the current optical transmittance value. Biofuels produce peroxides, oxide, polymerization products and so on in the process of degradation and change in color as the proportions of these compounds gradually change. Thus, since the degradation index value can be increased as the color indicating the degradation of the biofuel changes, the degree of degradation of the biofuel can be determined with high accuracy.

The degradation index value calculation means may calculate the degradation index value by accumulating the absolute value of the amount of change.

With this configuration, the degradation index value can be calculated by accumulating the absolute value of the amount of change in the optical transmittance or the color index value of the biofuel. In the process of degradation of biofuels, since the proportions of products such as peroxides, oxides and polymerization products and so on increase and decrease intricately, the optical transmittance or color index value may not change monotonously but may exhibit complex changes (increases and decreases). However, the amount of change in the optical transmittance or the color index value can be added to the degradation index value regardless of the direction of change in the optical transmittance or the color index value. Therefore, even in the above case, the degree of degradation of the biofuel can be determined with high accuracy.

The biofuel may have a temporal change characteristic of having at least one period during which the detection value from the detection means increases and at least one period during which the detection value decreases as the biofuel degrades with time.

When biofuel having a temporal change characteristic of having at least one period during which the optical transmittance or the color index value increases and at least one period during which the optical transmittance or the color index value decreases as the biofuel degrades with time is used, the degree of degradation of the biofuel can be determined with high accuracy.

The change amount calculation means may acquire the detection value at intervals shorter than the increase-decrease period of the detection value of the temporal change characteristic.

With the above configuration, the optical transmittance or the color index value can be acquired and the degradation index value can be calculated at intervals shorter than the increase-decrease period of the optical transmittance or the color index value of the temporal change characteristic of the biofuel. Therefore; changes in color of the biofuel can be grasped properly, and the degree of degradation of the biofuel can be determined with higher accuracy.

The device for detecting degradation of fuel may further include: fuel degradation determination means for determining that the biofuel has degraded when the degradation index value exceeds a predetermined value; and warning means for providing the driver with a warning when it is determined that the biofuel has degraded.

With this configuration, when it is determined that the biofuel has degraded, a warning can be provided to the driver. Therefore, since it is possible to surely urge the driver to take an countermeasure such as replacement of fuel, the fuel system parts and so on can be prevented from being damaged and the fuel system parts can be reliably protected.

The device for detecting degradation of fuel may further include: combustion state compensation means for performing at least one of a control operation to make the fuel injection pressure higher than usual, a control operation to make the fuel injection amount request value greater than usual and a control operation to heat the fuel to be supplied to the internal combustion engine based on the degradation index value.

Biofuels increase in viscosity as degradation proceeds. High viscosity biofuel makes it difficult for the fuel injectors to inject it and may result in a decrease in fuel injection amount or improper fuel spray. However, when the above control operation is performed, a decrease in fuel injection amount or improper fuel spray can be prevented more reliably.

The degradation index value calculation means may include determination means for determining whether or not the amount of change is due to measurement variation when the amount of change is smaller than a predetermined value; and addition selection means for allowing the amount of change to be added to the degradation index value when the determination means determines that the amount of change is not due to measurement variation and inhibiting the amount of change from being added to the degradation index value when the determination means determines that the amount of change is due to measurement variation.

With this configuration, when the amount of change in the optical transmittance or the color index value is smaller than a predetermined value, it is determined whether or not the amount of change is due to measurement variation. When it is determined that the amount of change is due to measurement variation, the amount of change is not added to the degradation index value. Therefore, even when the measurement values of the optical transmittance or the color index value includes variation, the degradation index value can be calculated more properly. As a result, the degradation of biofuel can be determined with higher accuracy.

A third aspect of the present invention relates to a method for detecting degradation of fuel for an internal combustion engine. The method for detecting degradation of fuel includes: a step of detecting an optical transmittance of biofuel stored in a fuel supply device of an internal combustion engine; a step of acquiring the optical transmittance periodically and calculating the amount of change from the previous optical transmittance value to the current optical transmittance value; and a step of calculating a degradation index value indicating the degree of degradation of the biofuel by accumulating the amount of change.

A fourth aspect of the present invention relates to a method for detecting degradation of fuel for an internal combustion engine. The method for detecting degradation of fuel includes: a step of detecting a color index value as an index of the color of biofuel stored in a fuel supply device of an internal combustion engine; a step of acquiring the color index value periodically and calculating the amount of change from the previous color index value to the color index value; and a step of calculating a degradation index value indicating the degree of degradation of the biofuel by accumulating the amount of change.

BRIEF DESCRIPTION OF THE DRAWINGS

The foregoing and further objects, features and advantages of the invention will become apparent from the following description of exemplary embodiments with reference to the accompanying drawings, wherein like numerals are used to represent like elements and wherein.

DETAILED DESCRIPTION OF EMBODIMENTS

Figure 1:
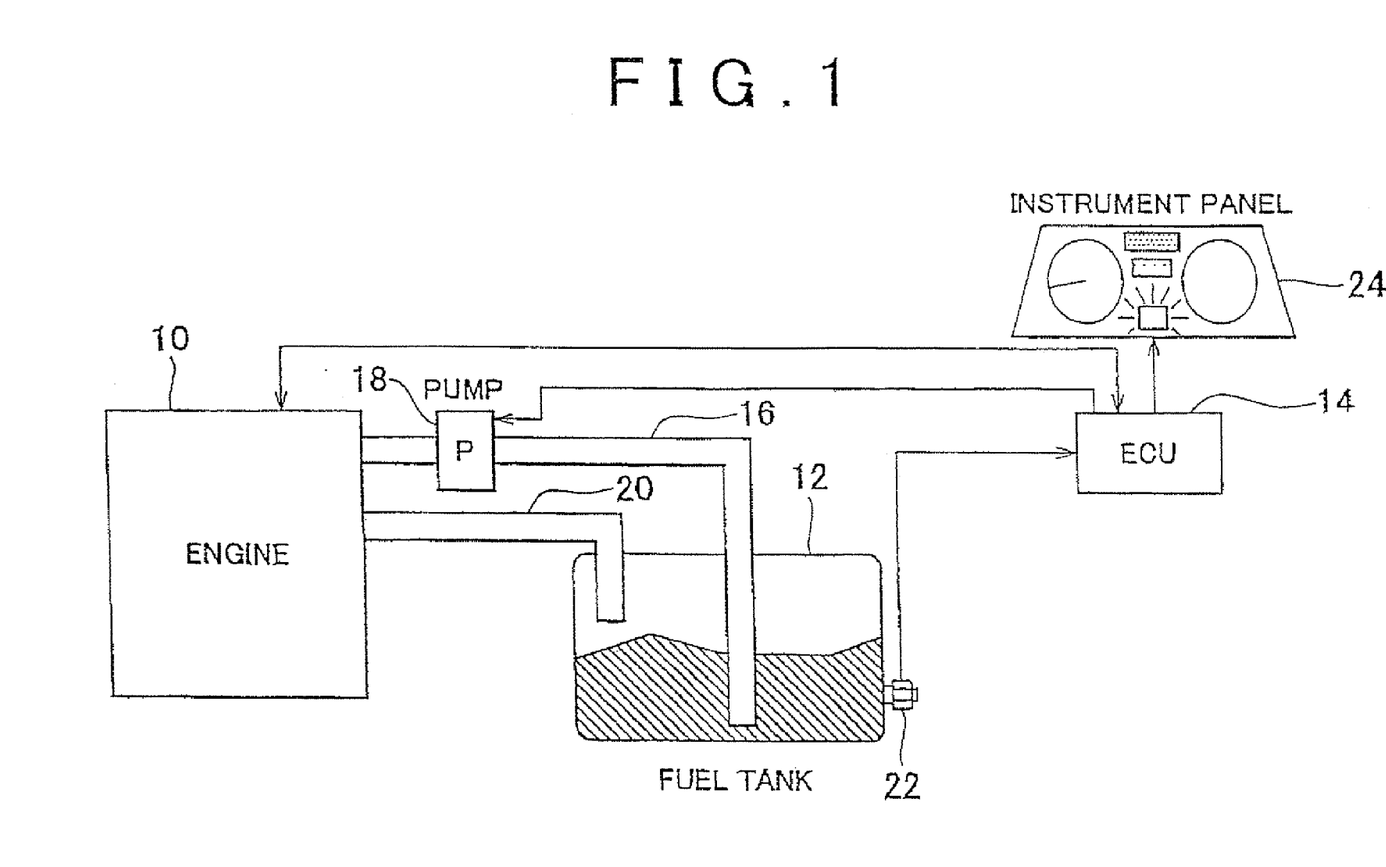
FIG. 1 is a view illustrating the system configuration of a first embodiment of the present invention.

FIG. 1 is a view illustrating the system configuration of a first embodiment of the present invention. As shown in FIG. 1, the system of this embodiment has an internal combustion engine 10 mounted in a vehicle; a fuel tank 12; and an ECU (Electronic Control Unit) 14 that controls the internal combustion engine 10. In this embodiment, the internal combustion engine 10 is a diesel engine.

The internal combustion engine 10 can be operated by using biofuel. The biofuel may be either 100% biomass-derived fuel produced from biomass or mixed fuel of biomass-derived fuel and other fuel.

The biofuel in the fuel tank 12 is fed through a fuel pipe 16 to a fuel pump 18 and pressurized therein, and is supplied to the internal combustion engine 10. The biofuel supplied to the internal combustion engine 10 is injected into cylinders from fuel injectors (not shown) provided for each of the cylinders. A portion of the biofuel supplied to the internal combustion engine 10 is returned to the fuel tank 12 through a fuel return pipe 20.

The fuel tank 12 is provided with a transmittance sensor 22 capable of detect the optical transmittance (optical transmission loss) of the biofuel in the fuel tank 12. In this embodiment, the transmittance sensor 22 has a light source that emits visible light (white light); a light guiding member that irradiates the biofuel with the light from the light source; and a sensor element that receives the light having passed through the biofuel and converts the light into electric energy, and is capable of detecting the optical transmittance of the biofuel for the visible light. The transmittance sensor 22 does not necessarily have to be on the fuel tank 12, and may be placed at some point on the fuel pipe 16.

The actuators such as the fuel pump 18 and the fuel injectors and sensors such as the transmittance sensor 22 are electrically connected to an ECU 14. Also, a display device in the instrument panel 24 in front of the driver's seat is electrically connected to the ECU 14.

Biofuels contain compounds having an unsaturated bond (double bond). The compounds easily undergo oxidation and polymerization reactions. In biofuels, peroxides, oxides, polymerization products and so on are produced as such oxidation and polymerization reactions proceed and cause degradation of fuel properties. According to the findings of the inventors, each of the peroxides, oxides, polymerization products and so on has a unique color. Therefore, biofuels change in color (color of transmitted light) as the oxidation and polymerization reactions proceed.

For example, fatty acid methyl ester fuel made from rapeseed oil (which is hereinafter referred to as "RME fuel") changes in color as follows, as the oxidation reaction proceeds according to the findings of the inventors: yellow→light yellow→dark yellow.

The changes in color of RME fuel is believed to be attributed to the phenomenon described below. The oxidation of substances like biofuel proceeds through the following steps; starting substance→peroxide→oxide (acid).

Figure 2:
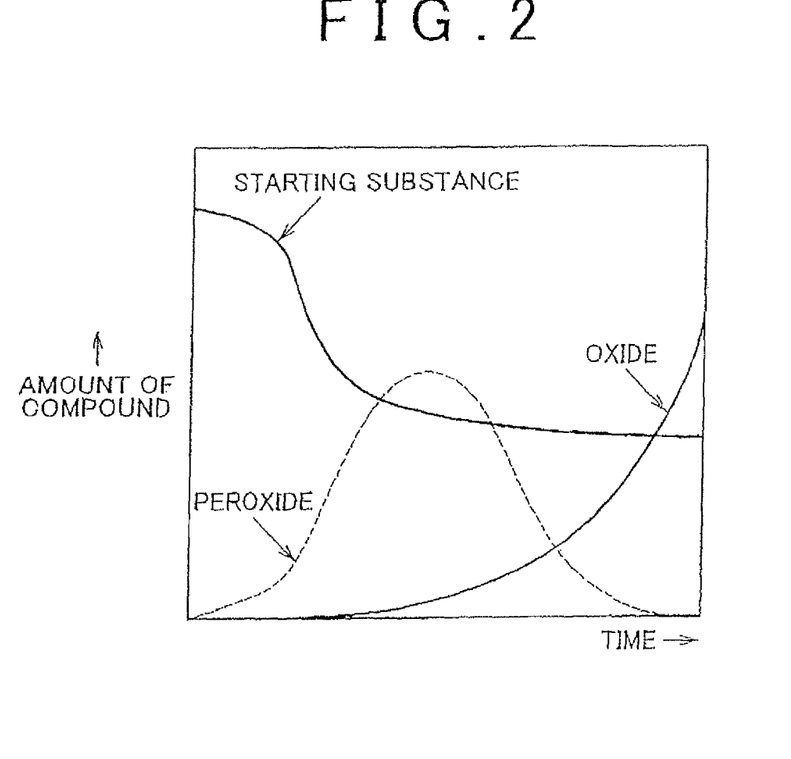
FIG. 2 is a view showing changes in the proportions of components with progress of oxidation of biofuel.

FIG. 2 is a view showing changes in the proportions of components with progress of oxidation of biofuel which proceeds through the above steps. As shown in FIG. 2, since starting substance first turns into peroxide as oxidation proceeds with time, the proportion of starting substance decreases and the proportion of peroxide increases. As time further progresses, the proportion of peroxide decreases and the proportion of oxide increases since the peroxide turn into oxide.

It is believed that the above RME fuel changes in color as described before since the colors of the starting substance, peroxide and oxide are yellow, light yellow and dark yellow, respectively. That is, it is believed that the RME fuel is yellow when it is fresh since the proportion of starting substance is high, turn light yellow as the proportion of peroxide increases, and then turns dark yellow as the proportion of oxide increases.

As described above, biofuels change in color in accordance with the progress oxidation and polymerization reactions, which lead to degradation thereof. It is, therefore, thought to be a good idea to detect degradation of biofuel by detecting changes in color of the biofuel with an optical sensor or the like.

Figure 3:
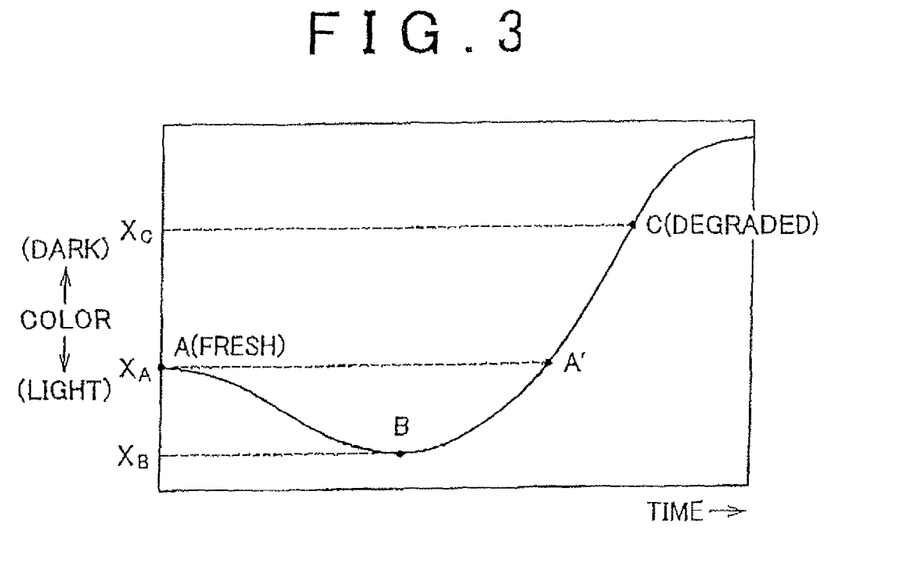
FIG. 3 is a view showing changes in color of biofuel.

FIG. 3 is a view showing a graph having a horizontal axis representing time and a vertical axis representing the color density (optical transmittance) of a biofuel. In the system of this embodiment, the color density of the biofuel in the fuel tank 12 can be detected by the transmittance sensor 22. That is, the biofuel has a lower optical transmittance X as the color of the biofuel is darker, and the biofuel has a higher optical transmittance X as the color of the biofuel is lighter.

As shown in FIG. 3, as oxidation proceeds from the fresh state (point A in FIG. 3), the above RMF fuel and so on becomes lighter and lighter in color (to point B in FIG. 3). After that, the fuel becomes darker and darker in color until it is darker than it is when it is fresh (point C in FIG. 3). In this embodiment, when oxidation proceeds to the level of point C in FIG. 3, it is determined that the biofuel has degraded beyond the acceptable limit and a warning is provided to the driver.

In the case shown in FIG. 3, the optical transmittance X of the biofuel first increases from an initial value $X_A$ of fresh condition, and takes a maximum value $X_B$ at point B. After that, the optical transmittance X of the biofuel decreases to a value which is smaller than the initial value $X_A$ ($X_C$, for example). Since the optical transmittance X of the biofuel changes as described above, the degree of degradation of the biofuel cannot be determined accurately if the value of the optical transmittance X itself detected by the transmittance sensor 22 is used as the basis for the determination. For example, at point A' in FIG. 3, which is close to point C at which the biofuel is determined to have degraded, the biofuel has degraded by a significant level but the biofuel has an optical transmittance X almost equal to the initial value $X_A$ of fresh condition. Thus, when the value of the optical transmittance X detected by the transmittance sensor 22 is compared with a determination value (the initial value $X_A$, for example), the degree of degradation of the biofuel cannot be determined accurately.

Figure 4:
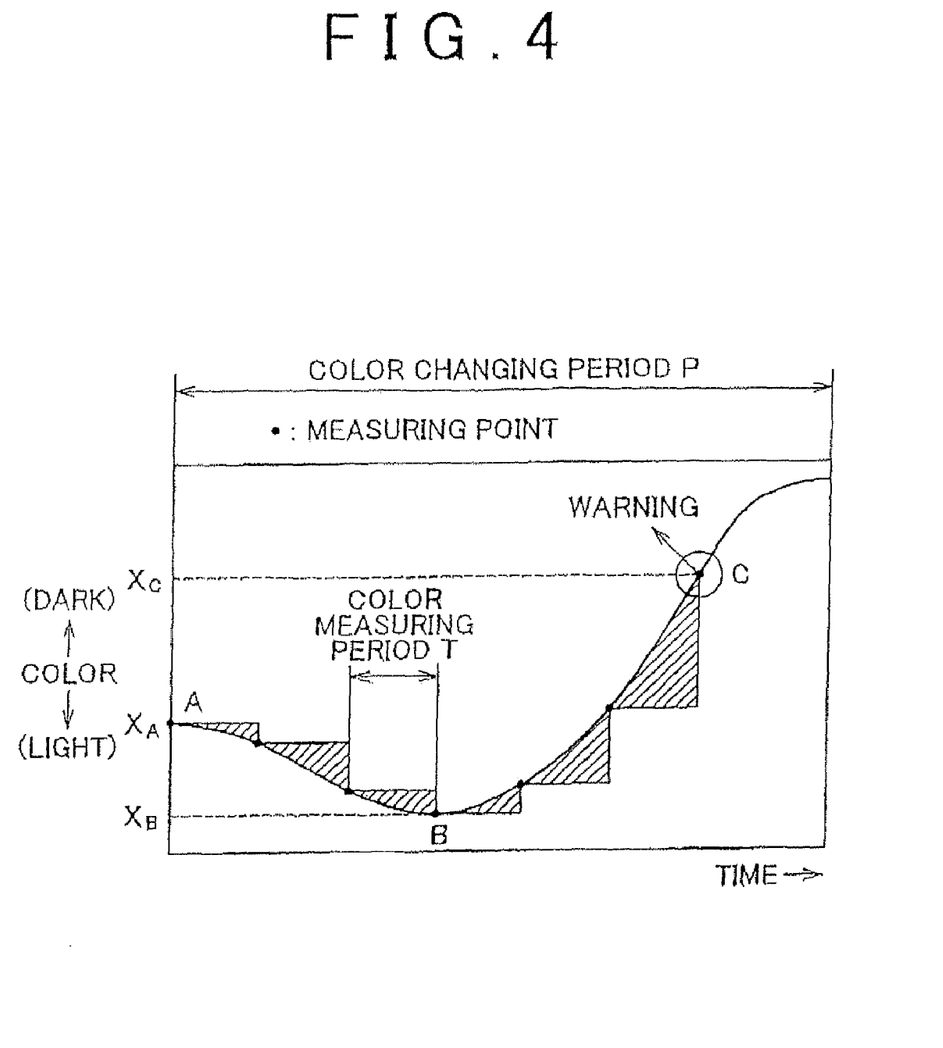
FIG. 4 is a view illustrating a method for calculation of the degree of degradation of biofuel in the first embodiment of the present invention.

Therefore, in this embodiment, the optical transmittance X of the biofuel is obtained periodically and a degradation degree Y as an index of the degree of degradation of the biofuel is calculated by accumulating the amount of change in the optical transmittance X (the absolute value of the difference from the previous value). FIG. 4 is a view illustrating the method for calculation of the degradation degree Y. In this embodiment, as shown in FIG. 4, the transmittance sensor 22 acquires the optical transmittance X of the biofuel once every predetermined color measuring period T (in the following description, once every seven days; that is, color measuring period T=seven days). The color measuring period T is preferably sufficiently shorter than the color changing period P of the biofuel. In the example shown in FIG. 4, the period in which the color of the biofuel first becomes lighter and then becomes dark again corresponds to the color changing period P.

The degradation degree Y is calculated by accumulating the absolute value of the difference between a newly acquired optical transmittance $X_t$ and an optical transmittance $X_{t-7}$ acquired one color measuring period before (seven days before). That is, the degradation degree Y is calculated by the equation:

$$Y=\Sigma |X_t - X_{t-7}| \tag{1}$$

The degradation degree Y which is calculated based on above equation (1) (the area of the hatched parts in FIG. 4), becomes greater as the degradation of the biofuel proceeds with time. Then, when the degradation of the biofuel proceeds to point C, at which a warning must be provided to the driver, the degradation degree Y reaches a certain value $Y_L$. Therefore, when the value $Y_L$ is defined as a threshold value, the degradation of the biofuel can be determined accurately by comparing the degradation degree Y of the biofuel and the threshold value $Y_L$.

Figure 5:
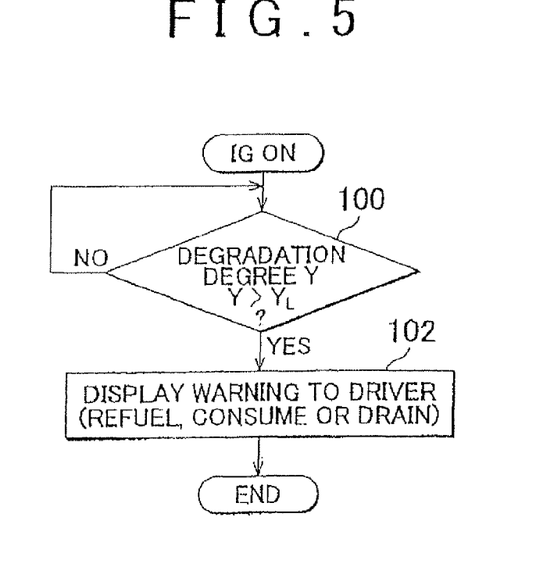
FIG. 5 is a flowchart of a routine which is executed in the first embodiment of the present invention.

[Specific operation in first embodiment] FIG. 5 is a flowchart of a routine that the ECU 14 executes to accomplish the above function in this embodiment. This routine is executed when the ignition switch of the vehicle is turned on. According the routine shown in FIG. 5, the value of the degradation degree Y of the biofuel in the fuel tank 12 is read, and the degradation degree Y and a predetermined degradation degree threshold value $Y_L$ are compared (step 100).

Let it be assumed that the ECU 14 acquires the optical transmittance X detected by the transmittance sensor 22 once every seven days and calculates the degradation degree Y based on equation (1). When the fact the fuel tank 12 is refilled with biofuel is detected, the ECU 14 resets the degradation degree Y and measures an initial value $X_0$ of the optical transmittance of the newly supplied biofuel. The method for detecting whether or not the fuel tank 12 is refilled is not particularly limited. For example, it can be detected based on the fuel level gauge of the fuel tank 12.

If the degradation degree Y is equal to or lower than the threshold value $Y_L$ in step 100, it can be determined that the degree of degradation of the biofuel in the fuel tank 12 is within an acceptable limit.

If the degradation degree Y is higher than the threshold value $Y_L$ in step 100, it can be determined that the degree of degradation of the biofuel in the fuel tank 12 is beyond the acceptable limit. In this case, a warning to urge the driver to take some action (to refill the fuel to dilute the remaining fuel, to consume the remaining fuel as soon as possible, to drain the remaining fuel in the fuel tank 12 and supply the fuel with fresh fuel, etc.) is displayed on a predetermined display part of the instrument panel 24 (step 102). Therefore, the degraded biofuel is prevented from being supplied to the internal combustion engine 10, and adverse effects such as damages to fuel system parts can be prevented.

Biofuels can increase in viscosity as the degradation proceeds because of polymerization or other reasons. High viscosity biofuel makes it difficult for the fuel injectors to inject the fuel and may result in a decrease in fuel injection amount or improper fuel spray. Although it is desirable not to use biofuel with a degradation degree Y beyond the threshold value $Y_L$, a combustion state compensation control operation as described below may be performed in this embodiment as a temporary solution before replacement of the fuel or to prevent engine performance deterioration when the degradation degree Y has increased to just below the threshold value $Y_L$.

Figure 6:
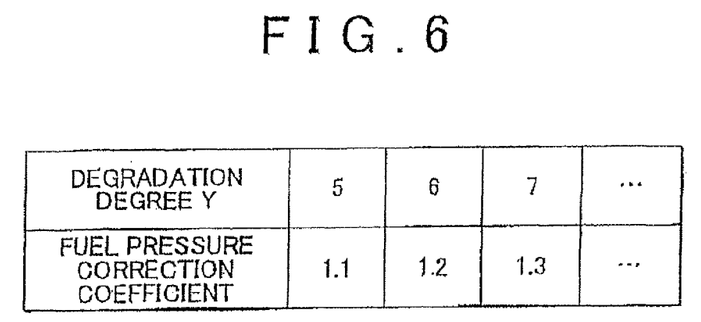
FIG. 6 is a view showing a map for use in calculation of a fuel pressure correction coefficient based on the degree of degradation of biofuel.

(1) A fuel injection pressure increase control operation is used to control the fuel pump 18 and so on to increase the fuel injection pressure by multiplying the requested injection pressure by a fuel pressure correction coefficient based on the calculated degradation degree Y. FIG. 6 is a view showing an example of a map for use in calculation of the fuel pressure correction coefficient based on the degradation degree Y. According to the map, when the degradation degree Y is 5, 1.1 is calculated as the fuel pressure correction coefficient, for example. Thus, in this case, under the condition where a fuel injection pressure of 80 MPa is usually selected, for example, the control is adjusted so that the fuel injection pressure, will be 88 MPa, which is obtained by multiplying the fuel injection pressure by a fuel pressure correction coefficient of 1.1. With the fuel injection pressure increase control operation, since improper fuel spray can be reliably prevented by controlling the fuel injection pressure to be higher as the degradation degree Y of the biofuel is higher, i.e., as the viscosity of the biofuel is higher, insufficient combustion can be prevented.

Figure 7:
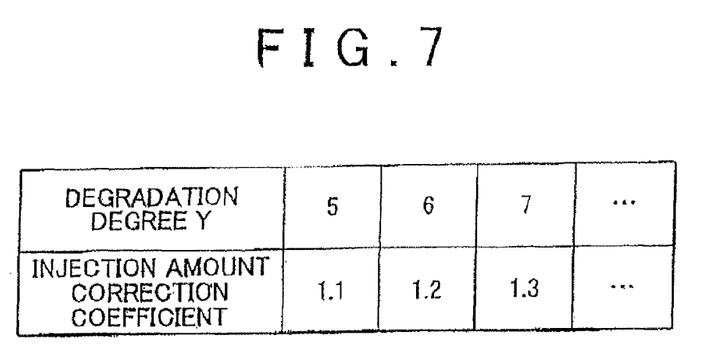
FIG. 7 is a view showing a map for use in calculation of an injection amount correction coefficient based on the degree of degradation of biofuel.

(2) fuel injection amount request value increase control operation is used to increase the fuel injection amount request value by multiplying the fuel injection amount request value by an injection amount correction coefficient based on the calculated degradation degree Y. FIG. 7 is a view illustrating an example of the map for use in calculation of the injection amount correction coefficient based on the degradation degree Y. According to the map, when the degradation degree Y is 5, 1.1 is calculated as the injection amount correction coefficient, for example. In this case, under the driving condition where a fuel injection amount request value of 10 mm³/st is usually selected, for example, 11 mm³/st obtained by multiplying the fuel injection amount request value by an injection amount correction coefficient of 1.1 is determined as the fuel injection amount request value. With the fuel injection amount request value increase control operation, since a decrease in the actual fuel injection amount can be reliably prevented by controlling the fuel injection amount request value to be greater as the degradation degree Y of the biofuel is higher, i.e., as the viscosity of the biofuel is higher, a decrease in engine torque can be prevented.

(3) fuel heating control operation is used to improve the fluidity of the biofuel by heating the biofuel to be supplied to the internal combustion engine 10 to raise the temperature thereof when the calculated degradation degree Y exceeds a predetermined reference value. With this control operation, adverse effects due to an increase in the viscosity of the biofuel can be avoided, and improper fuel spray can be reliably prevented. The method for heating the biofuel is not particularly limited. For example, a heater may be installed in the fuel pipe 16 or in the fuel injectors, or the high-temperature fuel flowing through the fuel return pipe 20 may be allowed to exchange heat with the fuel flowing through the fuel pipe 16.

The combustion state compensation control operations (1) to (3) may be used individually or in combination. Also, one or more of control operations similar to the above (1) to (3) may be applied to the control of the fuel additive injector of the exhaust system.

In the first embodiment described above, the fuel tank 12, the fuel pipe 16 and the fuel pump 18 may be regarded as the "fuel supply means" of the present invention, the transmittance sensor 22 as the "detection means" of the present invention, the degradation degree Y as the "degradation index value" of the present invention, the characteristic shown in FIG. 3 as the "temporal change characteristic" of the present invention, and the color changing period P shown in FIG. 4 as the "detection value increase-decrease period" of the present invention. For the ECU 14 to acquire the optical transmittance $X_t$ of the biofuel once every color measuring period T and calculate $|X_t-X_{t-T}|$ can be regarded as the operation of the "Change amount calculation means" in the present invention. To calculate the degradation degree Y based on equation (1) can be regarded as the operation of the "degradation index value calculation means" in the present invention. To perform step 100 can be regarded as the operation of the "fuel degradation determination means" in the present invention. To perform step 102 can be regarded as the operation of the "warning means" in the present invention. To execute at least one of the combustion state compensation control operations (1) to (3) is implemented can be regarded as the operation of the "combustion state compensation means" in the present invention.

While the changes in color of biofuel is detected based on the amount of change in the optical transmittance for a visible light detected by the transmittance sensor 22 in this embodiment, the method for detecting changes in color of biofuel in the present invention is not limited thereto. In the present invention; a color index value detection means (spectral transmittance meter, color difference meter, colorimeter, or spectrophotometric colorimeter, for example) for detecting a color index value of biofuel (spectral transmittance at a specific wavelength, value obtained by quantifying the hue of the transmitted light, value obtained by quantifying the saturation of the transmitted light, or value obtained by quantifying the brightness of the transmitted light, for example) may be provided and the changes in color of biofuel may be detected based on the amount of change in the color index value. That is, a color index value as described above may be used instead of optical transmittance in the present invention.

Figure 8A:
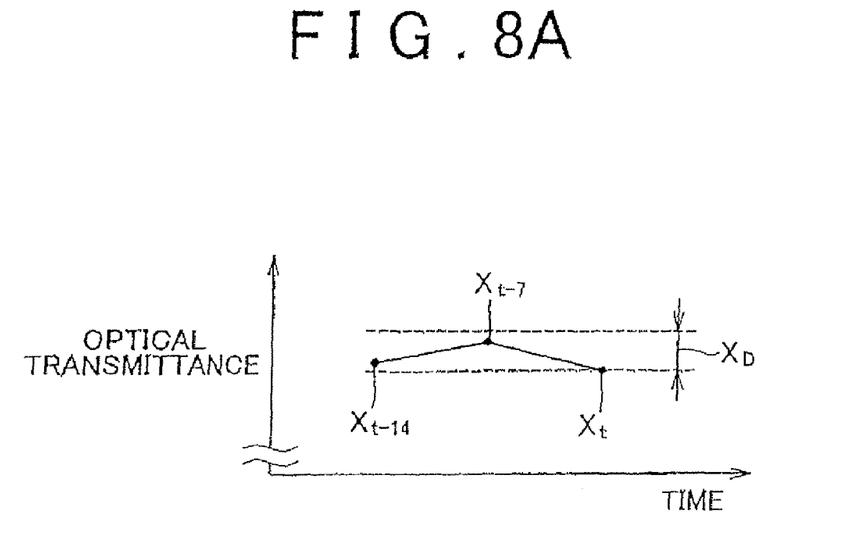
FIGS. 8A and 8B are views illustrating a method for calculation of the degree of degradation of biofuel in a second embodiment of the present invention.
Figure 8B:
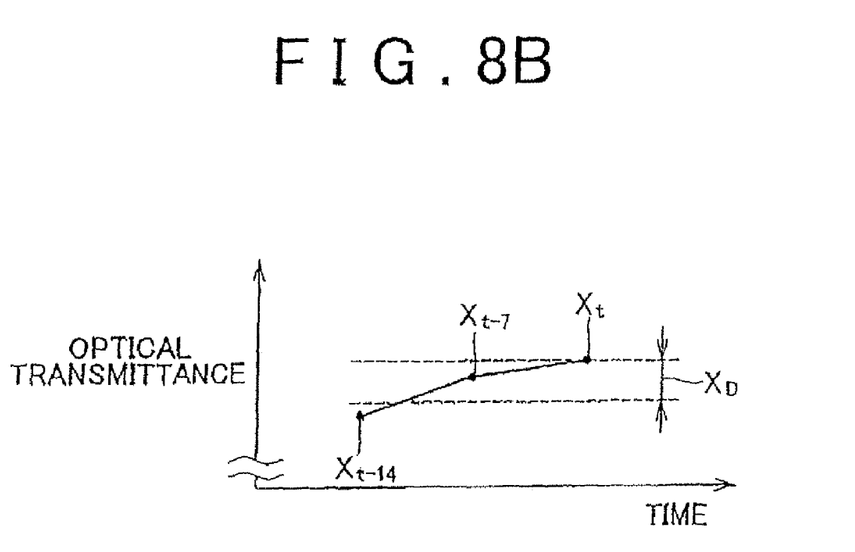
Figure 9:
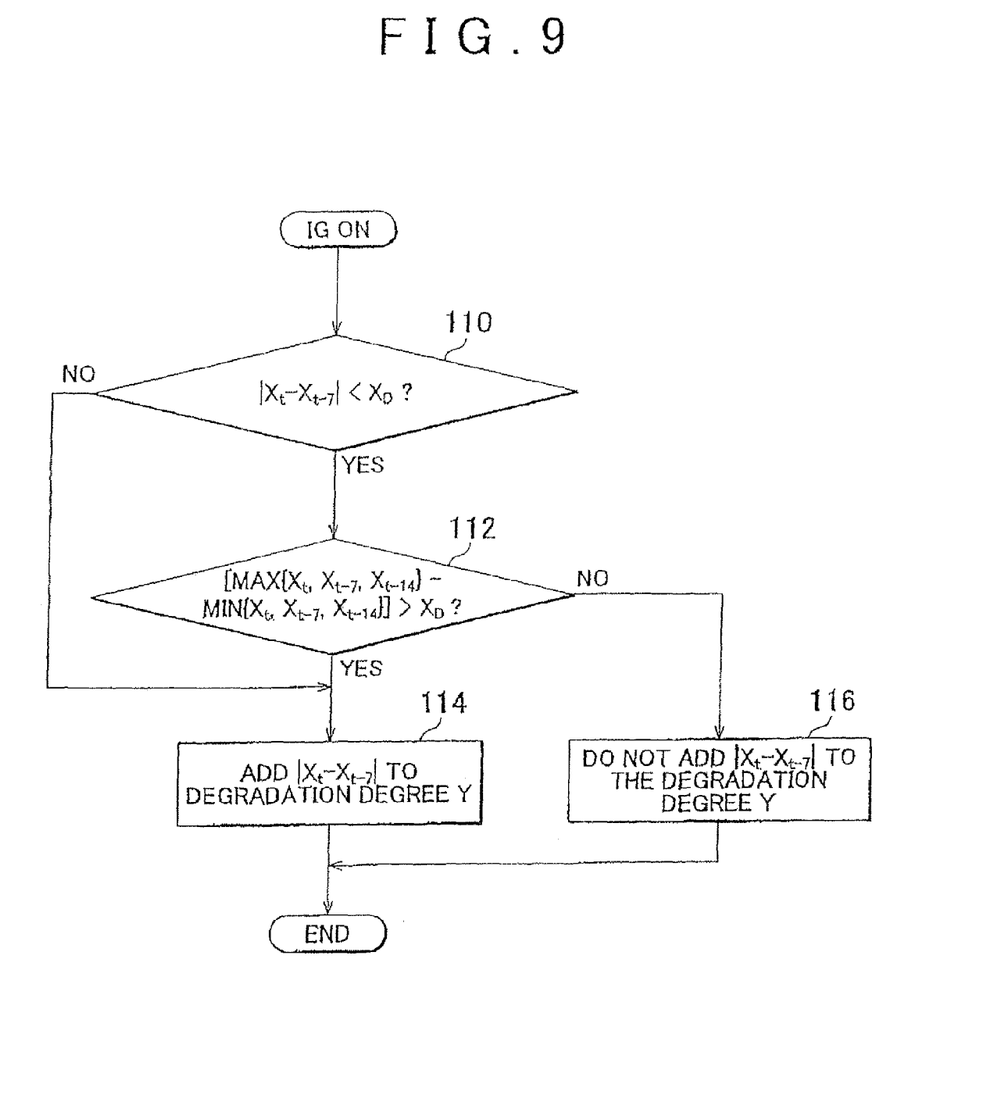
FIG. 9 is a flowchart of a routine which is executed in the second embodiment of the present invention.

Referring to FIG. 8 and FIG. 9, a second embodiment of the present invention is next described. In the following description, emphasis is placed on the differences from the above embodiment, and the description of the same things are abbreviated or omitted. As the hardware configuration of this embodiment, the hardware configuration shown in FIG. 1 may be used as in the first embodiment.

In this embodiment, the optical transmittance $X_t$ of the biofuel is acquired once in seven days and the degradation degree Y of the biofuel is calculated based on the amount of change $|X_t-X_{t-7}|$ from the previous value $X_{t-7}$ as in the first embodiment. In this embodiment, however, the degradation degree Y is calculated according to the rule described below.

The measurement values of the optical transmittance $X_t$ of the biofuel may include variation due to measurement error and so on. Thus, when the amount of change $|X_t-X_{t-7}|$ in optical transmittance is very small, the biofuel may have had no change in color in reality. Therefore, if $|X_t-X_{t-7}|$ is always added to the degradation degree Y without discrimination when $|X_t-X_{t-7}|$ is very small, the degradation of the biofuel may be overestimated. On the other hand, if $|X_t-X_{t-7}|$ is not added to the degradation degree Y without discrimination when $|X_t-X_{t-7}|$ is very small, the degradation of biofuel may not be detected accurately if the speed of change in color of the biofuel is slow.

Therefore, in this embodiment, the measurement values of the optical transmittance $X_t$ obtained in the last several measurements are stored, and, when $|X_t-X_{t-7}|$ is very small, the tendency of the change in the optical transmittance $X_t$ is determined based on the measurement values obtained in the last several measurements and then it is determined whether to add $|X_t-X_{t-7}|$ to the degradation degree Y.

FIG. 8 is, a view illustrating the determination method in detail, and FIG. 9 is a flowchart of a routine that the ECU 14 executes to calculate the degradation degree Y based on the determination method. The routine shown in FIG. 9 is executed every time the optical transmittance $X_1$ is measured once every seven days.

According to the routine shown in FIG. 9, it is first determined whether or not the absolute value of the difference $|X_t-X_{t-7}|$ between the current measurement value $X_t$ and the previous measurement value $X_{t-7}$ (obtained seven days before) is smaller than a variation threshold value $X_D$ (step 110). The variation threshold value $X_D$ is previously set based on the range of measurement error with which the optical transmittance $X_t$ can be measured.

If the determination in step 110 is negative, that is, if it is determined that $|X_t-X_{t-7}| \geqq X_D$, it can be determined that the amount of change $|X_t-X_{t-7}|$ in the optical transmittance detected this time may be attributed not to variation due to measurement error or the like but to an actual change in color of the biofuel. In this case, the current amount of change $|X_t-X_{t-7}|$ is added to the degradation degree Y (step 114).

If the determination in step 110 is positive, that is, if it is determined that $|X_t-X_{t-7}|<X_D$, it can be determined that the amount of change $|X_t-X_{t-7}|$ in the optical transmittance detected this time may be attributed to variation due to measurement error or the like. In this case, it is next determined whether or not the difference between the maximum value MAX$\{X_1, X_{t-7}, X_{t-14}\}$ and the minimum value MIN$\{X_t, X_{t-7}, X_{t-14}\}$ of the current measurement value $K_t$, the previous measurement value $X_{t-7}$ and the measurement value $X_{1-14}$ before the previous one (obtained 14 days before) is greater than $X_D$ (step 112).

FIG. 8A shows an example in which the determination in step 112 is negative. As shown in the drawing, if the difference between the maximum value MAX$\{X_t, X_{t-7}, t_{t-14}\}$ and the minimum value MIN$\{X_t, X_{t-7}, X_{1-14}\}$ of the three measurement values is equal to or smaller than $X_D$, it can be determined that the recent change in the optical transmittance $X_t$ is highly likely to be within the range of variation. Thus, in this case, the current amount Of change $|X_t-X_{t-7}|$ is not added to the degradation degree Y (step 116).

FIG. 8B shows an example in which the determination in step 112 is positive. As shown in the drawing, if the difference between the maximum value MAX$\{X_t, X_{t-7}, X_{t-14}\}$ and the minimum value MIN$\{X_t, X_{t-7}, X_{1-14}\}$ of the three measurement values is greater than $X_D$, since the recent change in the optical transmittance $X_t$ has a tendency to shift in one direction, it can be determined that it is highly likely that the color of the biofuel has actually changed. Thus, in this case, the current amount of change $|X_t-X_{t-7}|$ is added to the degradation degree Y (step 114).

According to the operation of the routine shown in FIG. 9, even if the measurement values of the optical transmittance include variation, the degradation degree Y can be calculated more properly. Therefore, the degradation of biofuel can be determined with higher accuracy.

In the second embodiment described above, for the ECU 14 to perform the operation of the routine shown in FIG. 9 can be regarded as the operation of the "degradation index value calculation means" in the present invention, to perform steps 110 and 112 as the operation of the "determination means" in the present invention, and to perform steps 114 and 116 as the operation of the "addition selection means" of the present invention.

The invention claimed is:

1. A device for detecting degradation of fuel for an internal combustion engine, comprising:
    fuel supply means for supplying biofuel, namely either 100% biomass-derived fuel produced from biomass or mixed fuel of biomass-derived fuel and other fuel, to an internal combustion engine;
    detection means for detecting an optical transmittance of the biofuel stored in the fuel supply means;
    change amount calculation means for acquiring the optical transmittance periodically and calculating the amount of change from the previous optical transmittance value to the current optical transmittance value; and
    degradation index value calculation means for calculating a degradation index value indicating the degree of degradation of the biofuel by accumulating the amount of change.

2. A device for detecting degradation of fuel for an internal combustion engine, comprising:
    fuel supply means for supplying biofuel, namely either 100% biomass-derived fuel produced from biomass or mixed fuel of biomass-derived fuel and other fuel, to an internal combustion engine;
    detection means for detecting a color index value as an index of the color of biofuel stored in the fuel supply means;
    change amount calculation means for acquiring the color index value periodically and calculating the amount of change from the previous color index value to the current color index value; and
    degradation index value calculation means for calculating a degradation index value indicating the degree of degradation of the biofuel by accumulating the amount of change.

3. The device for detecting degradation of fuel according to claim 1, wherein the degradation index value calculation means calculates the degradation index value by accumulating the absolute value of the amount of change.

4. The device for detecting degradation of fuel according to claim 1, wherein the biofuel has a temporal change characteristic of having at least one period during which the detection value from the detection means increases and at least one period during which the detection value decreases as the biofuel degrades with time.

5. The device for detecting degradation of fuel according to claim 4, wherein the change amount calculation means acquires the detection value at intervals shorter than the increase-decrease period of the detection value of the temporal change characteristic.

6. The device for detecting degradation of fuel according to claim 1,
further comprising:
fuel degradation determination means for determining that the biofuel has degraded when the degradation index value exceeds a predetermined value; and
warning means for providing the driver with a warning when it is determined that the biofuel has degraded.

7. The device for detecting degradation of fuel according to claim 1,
further comprising combustion state compensation means for performing at least one of a control operation to make the fuel injection pressure higher than usual, a control operation to make the fuel injection amount request value greater than usual and a control operation to heat the fuel to be supplied to the internal combustion engine, based on the degradation index value.

8. The device for detecting degradation of fuel according to claim 1, wherein the degradation index value calculation means includes determination means for determining whether or not the amount of change is due to measurement variation when the amount of change is smaller than a predetermined value; and addition selection means for allowing the amount of change to be added to the degradation index value when the determination means determines that the amount of change is not due to measurement variation and inhibiting the amount of change from being added to the degradation index value when the determination means determines that the amount of change is due to measurement variation.

9. A method for detecting degradation of fuel for an internal combustion engine, comprising:
detecting an optical transmittance of biofuel, namely either 100% biomass-derived fuel produced from biomass or mixed fuel of biomass-derived fuel and other fuel, stored in a fuel supply device of an internal combustion engine;
acquiring the optical transmittance periodically and calculating the amount of change from the previous optical transmittance value to the current optical transmittance value; and
calculating a degradation index value indicating the degree of degradation of the biofuel by accumulating the amount of change.

10. A method for detecting degradation of fuel for an internal combustion engine, comprising:
detecting a color index value as an index of the color of biofuel, namely either 100% biomass-derived fuel produced from biomass or mixed fuel of biomass-derived fuel and other fuel, stored in a fuel supply device of an internal combustion engine;
acquiring the color index value periodically and calculating the amount of change from the previous color index value to the color index value; and
calculating a degradation index value indicating the degree of degradation of the biofuel by accumulating the amount of change.

11. A device for detecting degradation of fuel for an internal combustion engine, comprising:
a fuel supply device that supplies biofuel, namely either 100% biomass-derived fuel produced from biomass or mixed fuel of biomass-derived fuel and other fuel, to an internal combustion engine;
a detector that detects an optical transmittance of the biofuel stored in the fuel supply device; and
a controller that acquires the optical transmittance periodically and calculates a degradation index value indicating the degree of degradation of the biofuel by calculating the amount of change from the previous optical transmittance value to the current optical transmittance value and accumulating the amount of change.

12. A device for detecting degradation of fuel for an internal combustion engine, comprising:
a fuel supply device that supplies biofuel, namely either 100% biomass-derived fuel produced from biomass or mixed fuel of biomass-derived fuel and other fuel, to an internal combustion engine;
a detecting device that detects a color index value as an index of the color of biofuel stored in the fuel supply device;
a controller that acquires the color index value periodically and calculates a degradation index value indicating the degree of degradation of the biofuel by calculating the amount of change from the previous color index value to the current color index value and accumulating the amount of change.

13. The device for detecting degradation of fuel according to claim 2, wherein the degradation index value calculation means calculates the degradation index value by accumulating the absolute value of the amount of change.

14. The device for detecting degradation of fuel according to claim 2, wherein the biofuel has a temporal change characteristic of having at least one period during which the detection value from the detection means increases and at least one period during which the detection value decreases as the biofuel degrades with time.

15. The device for detecting degradation of fuel according to claim 2, further comprising:
fuel degradation determination means for determining that the biofuel has degraded when the degradation index value exceeds a predetermined value; and
warning means for providing the driver with a warning when it is determined that the biofuel has degraded.

16. The device for detecting degradation of fuel according to claim 2, further comprising combustion state compensation means for performing at least one of a control operation to make the fuel injection pressure higher than usual, a control operation to make the fuel injection amount request value greater than usual and a control operation to heat the fuel to be supplied to the internal combustion engine, based on the degradation index value.

17. The device for detecting degradation of fuel according to claim 2, wherein the degradation index value calculation means includes determination means for determining whether or not the amount of change is due to measurement variation when the amount of change is smaller than a predetermined value; and addition selection means for allowing the amount of change to be added to the degradation index value when the determination means determines that the amount of change is not due to measurement variation and inhibiting the amount of change from being added to the degradation index value when the determination means determines that the amount of change is due to measurement variation.

* * * * *